United States Patent
Smyth et al.

(10) Patent No.: US 8,127,763 B2
(45) Date of Patent: Mar. 6, 2012

(54) DRY POWDER INHALER WITH AEROELASTIC DISPERSION MECHANISM

(75) Inventors: Hugh C. Smyth, Albuquerque, NM (US); Charles R. Truman, Albuquerque, NM (US)

(73) Assignee: STC.UNM, Albuquerque, NM (US)

( * ) Notice: Subject to any disclaimer, the term of this patent is extended or adjusted under 35 U.S.C. 154(b) by 555 days.

(21) Appl. No.: 12/246,116

(22) Filed: Oct. 6, 2008

(65) Prior Publication Data

US 2009/0095294 A1    Apr. 16, 2009

Related U.S. Application Data (63) Continuation-in-part of application No. 11/713,180, filed on Mar. 2, 2007.

(60) Provisional application No. 60/778,878, filed on Mar. 3, 2006.

(51) Int. Cl.
*A61M 16/00* (2006.01)

(52) U.S. Cl. .......... 128/203.15; 128/203.12; 128/200.24

(58) Field of Classification Search ............. 128/200.24, 128/203.12, 203.15, 203.21, 203.19, 898; 222/80–83.5
See application file for complete search history.

(56) References Cited

U.S. PATENT DOCUMENTS

| | | | |
|---|---|---|---|
| 3,518,992 A | 7/1970 | Howell et al. | |
| 3,837,341 A | 9/1974 | Bell | |
| 3,858,583 A | 1/1975 | Hallworth et al. | |
| 3,888,253 A | 6/1975 | Watt et al. | |
| 3,948,264 A | 4/1976 | Wilke et al. | |
| 4,090,642 A * | 5/1978 | Baker | 222/94 |
| 4,735,358 A * | 4/1988 | Morita et al. | 239/1 |
| 4,907,583 A | 3/1990 | Wetterlin et al. | |
| 5,035,237 A * | 7/1991 | Newell et al. | 128/203.15 |
| 5,372,128 A | 12/1994 | Haber et al. | |
| 5,533,502 A | 7/1996 | Piper | |
| 5,653,227 A * | 8/1997 | Barnes et al. | 128/203.12 |
| 5,655,523 A | 8/1997 | Hodson et al. | |
| 5,692,496 A * | 12/1997 | Casper et al. | 128/203.15 |
| 5,740,793 A * | 4/1998 | Hodson et al. | 128/203.15 |
| 5,743,250 A * | 4/1998 | Gonda et al. | 128/200.14 |
| 5,860,419 A | 1/1999 | Davies et al. | |

(Continued)

FOREIGN PATENT DOCUMENTS

EP    1 291 032 A2    3/2003

OTHER PUBLICATIONS

Crowder et al. "2001: An Odyssey in Inhaler Formulation and Design." Pharmaceutical Technology, pp. 99-113 (Jul. 2001).

(Continued)

*Primary Examiner* — Annette Dixon
(74) *Attorney, Agent, or Firm* — Kilpatrick Townsend & Stockton LLP (57) ABSTRACT

A dry powder inhaler for delivering medicament to a patient includes a housing defining a chamber for receiving a dose of powdered medicament, an inhalation port in fluid communication with the chamber, at least one airflow inlet providing fluid communication between the chamber and an exterior of the housing, and an aeroelastic element in the chamber and associated with a dose of powdered medicament. A tensioning assembly is configured to apply a first amount of tension to the aeroelastic element such that the aeroelastic element is capable of vibrating in response to airflow through the chamber so as to aerosolize the dose of powdered medicament.

20 Claims, 6 Drawing Sheets

U.S. PATENT DOCUMENTS

| | | | |
|---|---|---|---|
| 6,029,663 | A | 2/2000 | Eisele et al. |
| 6,098,619 | A | 8/2000 | Britto et al. |
| 6,230,707 | B1 | 5/2001 | Horlin |
| 6,378,519 | B1 * | 4/2002 | Davies et al. ............ 128/203.21 |
| 6,425,888 | B1 * | 7/2002 | Embleton et al. ............. 604/290 |
| 6,626,173 | B2 | 9/2003 | Genova et al. |
| 6,655,380 | B1 | 12/2003 | Andersson et al. |
| 6,779,520 | B2 | 8/2004 | Genova et al. |
| 6,840,239 | B2 | 1/2005 | Myrman |
| 6,889,690 | B2 | 5/2005 | Crowder et al. |
| 7,284,553 | B2 | 10/2007 | Hochrainer |
| 7,401,713 | B2 * | 7/2008 | Ede et al. ........................ 222/83 |
| 2004/0094152 | A1 | 5/2004 | Harvey et al. |
| 2004/0206773 | A1 * | 10/2004 | Ede et al. ........................ 222/83 |
| 2004/0244794 | A1 | 12/2004 | Richards |
| 2005/0172962 | A1 | 8/2005 | Gumaste et al. |
| 2005/0194008 | A1 | 9/2005 | Andersson et al. |
| 2007/0209661 | A1 * | 9/2007 | Smyth et al. ............. 128/203.12 |
| 2007/0215149 | A1 | 9/2007 | King et al. |

OTHER PUBLICATIONS

Hickey et al. "A New Millenium for Inhaler Technology." Pharmaceutical Technology, vol. 21, pp. 116-125 (Jun. 1997).

Martonen et al. "Issues in Drug Delivery: Concepts and Practice." Respiratory Care, vol. 50, pp. 1228-1252 (Sep. 2005).

Peart et al. "New Developments in Dry Powder Inhaler Technology." American Pharmaceutical Review, vol. 4, pp. 37-45 (2001).

Prime et al. "Review of Dry Powder Inhalers." Advanced Drug Delivery Reviews, vol. 26, pp. 51-58 (1997).

Smyth et al. "Carriers in Drug Powder Delivery—Implications for Inhalation System Design." Am. J. Drug Deliv., vol. 3(2), pp. 117-132 (2005).

* cited by examiner

DRY POWDER INHALER WITH AEROELASTIC DISPERSION MECHANISM

CROSS-REFERENCE TO RELATED APPLICATIONS

This application is a continuation-in-part of U.S. application Ser. No. 11/713,180, entitled "Dry Powder Inhaler with Aeroelastic Dispersion Mechanism," filed on Mar. 2, 2007, pending, which claims the benefit of priority of U.S. provisional application No. 60/778,878, entitled "Dry Powder Inhaler with Aeroelastic Dispersion Mechanism," filed on Mar. 3, 2006, the contents of both of which are incorporated herein by reference in their entirety.

TECHNICAL FIELD

The present invention is directed generally to inhalers, for example, dry powder inhalers, and methods of delivering a medicament to a patient. More particularly, the present invention is directed to dry powder inhalers having an aeroelastic dispersion mechanism.

BACKGROUND

Dry powder inhalers ("DPIs") represent a promising alternative to pressurized meted dose inhaler ("pMDI") devices for delivering drug aerosols without using CFC propellants. See generally, Crowder et al., 2001: an Odyssey in Inhaler Formulation and Design, Pharmaceutical Technology, pp. 99-113, July 2001; and Peart et al., New Developments in Dry Powder Inhaler Technology, American Pharmaceutical Review, Vol. 4, n,3, pp. 37-45 (2001). Martonen et al. 2005 Respiratory Care, Smyth and Hickey American Journal of Drug Delivery, 2005.

Typically, the DPIs are configured to deliver a powdered drug or drug mixture that includes an excipient and/or other ingredients. Conventionally, many DPIs have operated passively, relying on the inspiratory effort of the patient to dispense the drug provided by the powder. Unfortunately, this passive operation can lead to poor dosing uniformity since inspiratory capabilities can vary from patient to patient, and sometimes even use-to-use by the same patient, particularly if the patient is undergoing an asthmatic attack or respiratory-type ailment which tends to close the airway.

Generally described, known single and multiple dose DPI devices use: (a) individual pre-measured doses, such as capsules containing the drug, which can be inserted into the device prior to dispensing; or (b) bulk powder reservoirs which are configured to administer successive quantities of the drug to the patient via a dispensing chamber which dispenses the proper dose. See generally, Prime et al., Review of Dry Powder Inhaler's, 26 Adv. Drug Delivery Rev., pp. 51-58 (1997); and Hickey et al., A New Millennium for Inhaler Technology, 21 Pharm. Tech., n. 6, pp. 116-125 (1997).

In operation, DPI devices desire to administer a uniform aerosol dispersion amount in a desired physical form (such as a particulate size) of the dry powder into a patient's airway and direct it to a desired deposit site. If the patient is unable to provide sufficient respiratory effort, the extent of drug penetration, especially to the lower portion of the airway, may be impeded. This may result in premature deposit of the powder in the patient's mouth or throat.

A number of obstacles can undesirably impact the performance of the DPI. For example, the small size of the inhalable particles in the dry powder drug mixture can subject them to forces of agglomeration and/or cohesion (i.e., certain types of dry powders are susceptible to agglomeration, which is typically caused by particles of the drug adhering together), which can result in poor flow and non-uniform dispersion. In addition, as noted above, many dry powder formulations employ larger excipient particles to promote flow properties of the drug. However, separation of the drug from the excipient, as well as the presence of agglomeration, can require additional inspiratory effort, which, again, can impact the stable dispersion of the powder within the air stream of the patient. Unstable dispersions may inhibit the drug from reaching its preferred deposit/destination site and can prematurely deposit undue amounts of the drug elsewhere.

A number of different inhalation devices have been designed to attempt to resolve problems attendant with conventional passive inhalers. For example, U.S. Pat. No. 5,655,523 discloses and claims a dry powder inhalation device which has a deagglormeration-aerosolization plunger rod or biased hammer and solenoid. U.S. Pat. No. 3,948,264 discloses the use of a battery-powered solenoid buzzer to vibrate the capsule to effectuate the efficient release of the powder contained therein. Those devices are based on the proposition that the release of the dry powder can be effectively facilitated by the use of energy input independent of patient respiratory effort.

U.S. Pat. No. 5,533,502 to Piper discloses and claims a powder inhaler using patient inspiratory efforts for generating a respirable aerosol. The Piper invention also includes a cartridge capable of rotating, holding the depressed wells or blisters defining the medicament holding receptacles. A spring-loaded carriage compresses the blister against conduits with sharp edges that puncture the blister to release the medication that is then entrained in air drawn in from the air inlet conduit so that aerosolized medication is emitted from the aerosol outlet conduit.

Crowder et al. describe a dry powder inhaler in U.S. Pat. No. 6,889,690 comprising a piezoelectric polymer packaging in which the powder for aerosolization is simulated using non-linear signals determined a priori for specific powders.

In recent years, dry powder inhalers (DPIs) have gained widespread use, particularly in the United States. Currently, the DPI market is estimated to be worth in excess of $4 billion. Dry powder inhalers have the added advantages of a wide range of doses that can be delivered, excellent stability of drugs in powder form (no refrigeration), ease of maintaining sterility, non-ozone depletion, and they require no press-and-breathe coordination.

There is great potential for delivering a number of therapeutic compounds via the lungs (see, for example, Martonen T., Smyth H D C, Isaccs K., Burton R., "Issues in Drug Delivery: Dry Powder Inhaler Performance and Lung Deposition": Respiratory Care. 2005, 50(9); and Smyth H D C, Hickey, A J, "Carriers in Drug Powder Delivery: Implications for Inhalation System Design," American Journal of Drug Delivery, 2005, 3(2), 117-132). In the search for non-invasive delivery of biologics (which currently must be injected), it was realized that the large highly absorptive surface area of the lung with low metabolic drug degradation, could be used for systemic delivery of proteins such as insulin. The administration of small molecular weight drugs previously administered by injection is currently under investigation via the inhalation route either to provide non-invasive rapid onset of action, or to improve the therapeutic ratio for drugs acting in the lung (e.g. lung cancer).

Gene therapy of pulmonary disease is still in its infancy but could provide valuable solutions to currently unmet medical needs. The recognition that the airways may provide a real opportunity for delivering biotech therapeutics in a non-invasive way was recently achieved with Exubera™, an inhaled insulin product. This product has obtained a recommendation for approval by US Food and Drug Administration and will lead to expanded opportunities for other biologics to be administered via the airways.

Key to all inhalation dosage forms is the need to maximize the "respirable dose" (particles with aerodynamic diameters <5.0 µm that deposit in the lung) of a therapeutic agent. However, both propellant-based inhalers and current DPI systems only achieve lung deposition efficiencies of less than 20% of the delivered dose. The primary reason why powder systems have limited efficiency is the difficult balancing of particle size (particles under 5 µm diameter) and strong interparticulate forces that prevent deaggregation of powders (strong cohesive forces begin to dominate at particle sizes <10 µm) (Smyth H D C., Hickey, A J., "Carriers in Drug Powder Delivery: Implications for inhalation System Design," American Journal of Drug Delivery, 2005, 3(2), 117-132). Thus, DPIs require considerable inspiratory effort to draw the powder formulation from the device to generate aerosols for efficient lung deposition (see FIG. 1 for an illustration of typical mechanism of powder dispersion for DPIs). Many patients, particularly asthmatic patients, children, and elderly patients, which are important patient groups for respiratory disease, are not capable of such effort. In most DPIs, approximately 60 L/min of airflow is required to effectively deaggregate the fine cohesive powder. All currently available DPIs suffer from this potential drawback.

Multiple studies have shown that the dose emitted from dry powder inhalers (DPI) is dependent on air flow rates (see Martonen T., Smyth H D C, Isaccs K., Burton R., "Issues in Drug Delivery: Dry Powder Inhaler Performance and Lung Deposition": Respiratory Care. 2005, 50(9)). Increasing airflow increases drug dispersion due to increases in drag forces of the fluid acting on the particle located in the flow. The Turbuhaler® device (a common DPI), is not suitable for children because of the low flow achieved by this patient group (see Martonen T., Smyth H D C, Isaccs K., Burton R., "Issues in Drug Delivery: Dry Powder Inhaler Performance and Lung Deposition": Respiratory Care. 2005, 50(9)).

Considerable intra-patient variability of inhalation rates has been found when patients inhale through two leading DPI devices. That inherent variability has prompted several companies to evaluate ways of providing energy in the inhaler (i.e. "active" DPIs). Currently, there is no active DPI commercially available. The active inhalers under investigation include technologies that use compressed air, piezoelectric actuators, and electric motors. The designs of those inhalers are very complex and utilize many moving parts and components. The complexity of those devices presents several major drawbacks including high cost, component failure risk, complex manufacturing procedures, expensive quality control, and difficulty in meeting specifications for regulatory approval and release (Food and Drug Administration).

Alternatively, powder technology provides potential solutions for flow rate dependence of DPIs. For example, hollow porous microparticles having a geometric size of 5-30 µm, but aerodynamic sizes of 1-5 µm require less power for dispersion than small particles of the same mass. This may lead to flow independent drug dispersion but is likely to be limited to a few types of drugs with relevant physicochemical properties.

Thus there are several problems associated with current dry powder inhaler systems including the most problematic issue: the dose a patient receives is highly dependent on the flow rate the patient can draw through the passive-dispersion device. Several patents describing potential solutions to this problem employ an external energy source to assist in the dispersion of powders and remove this dosing dependence on patient inhalation characteristics. Only one of these devices has made it to market or been approved by regulatory agencies such as the U.S. Food and Drug Administration. Even upon approval, it is likely that these complex devices will have significant costs of manufacture and quality control, which could have a significant impact on the costs of drugs to patients.

The present disclosure describes exemplary dry powder inhalers and associated single or multi-dose packaging, which holds the compound to be delivered for inhalation as a dry powder. These dry powder inhalers bridge the gap between passive devices and active devices. The inhalers are passive devices that operate using the energy generated by the patient inspiratory flow inhalation maneuver. However, the energy generated by airflow within the devices is focused on the powder by using oscillations induced by airflow across an aeroelastic element. In this way the inhalers can be "tuned" to disperse the powder most efficiently by adjusting the resonance frequencies of the elastic element to match the physicochemical properties of the powder. In addition, the airflow rate required to generate the appropriate oscillations within the device is minimized because some of the energy used to create the vibrations in the elastic element is pre-stored in the element in the form of elastic tension (potential energy). Inhaler performance may be tailored to the lung function of individual patients by modulating the elastic tension. Thus, even patients with poor lung function and those who have minimal capacity to generate airflow during inspiration will able to attain the flow rate required to induce oscillations in the elastic element.

SUMMARY OF THE INVENTION

An exemplary embodiment of the invention comprises a dry powder inhaler with an integrated assisted dispersion system that is adjustable according to the patients' inspiratory capabilities and the adhesive/cohesive nature of the powder. The inhaler comprises an aeroelastic element that flutters or oscillates in response to airflow through the inhaler. The aeroelastic element provides concentrated energy of the airflow driven by the patient into the powder to be dispersed. The aeroelastic element is preferably a thin elastic membrane held under tension that reaches optimal vibrational response at low flow rates drawn through the inhaler by the patient. The aeroelastic element is preferably adjustable according to the patient's inspiratory capabilities and the adhesive/cohesive forces within the powder for dispersal.

According to various aspects of the disclosure, a dry powder inhaler for delivering medicament to a patient includes a housing defining a chamber for receiving a dose of powdered medicament, an inhalation port in fluid communication with the chamber, at least one airflow inlet providing fluid communication between the chamber and an exterior of the housing, and an aeroelastic element in the chamber and associated with a dose of powdered medicament. A tensioning assembly is configured to apply a first amount of tension to the aeroelastic element such that the aeroelastic element is capable of vibrating in response to airflow through the chamber so as to aerosolize the dose of powdered medicament.

DETAILED DESCRIPTION

Figure 3A:
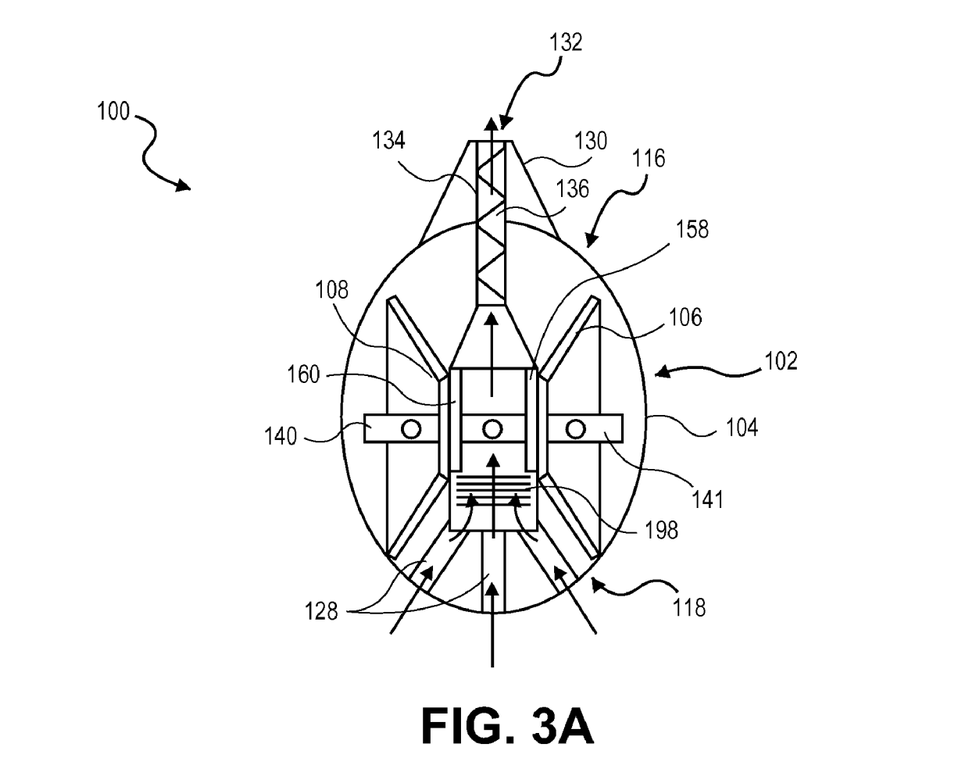
FIG. 3A is a schematic representation of a top cross-sectional view of an exemplary inhaler in accordance with various aspects of the disclosure.
Figure 3B:
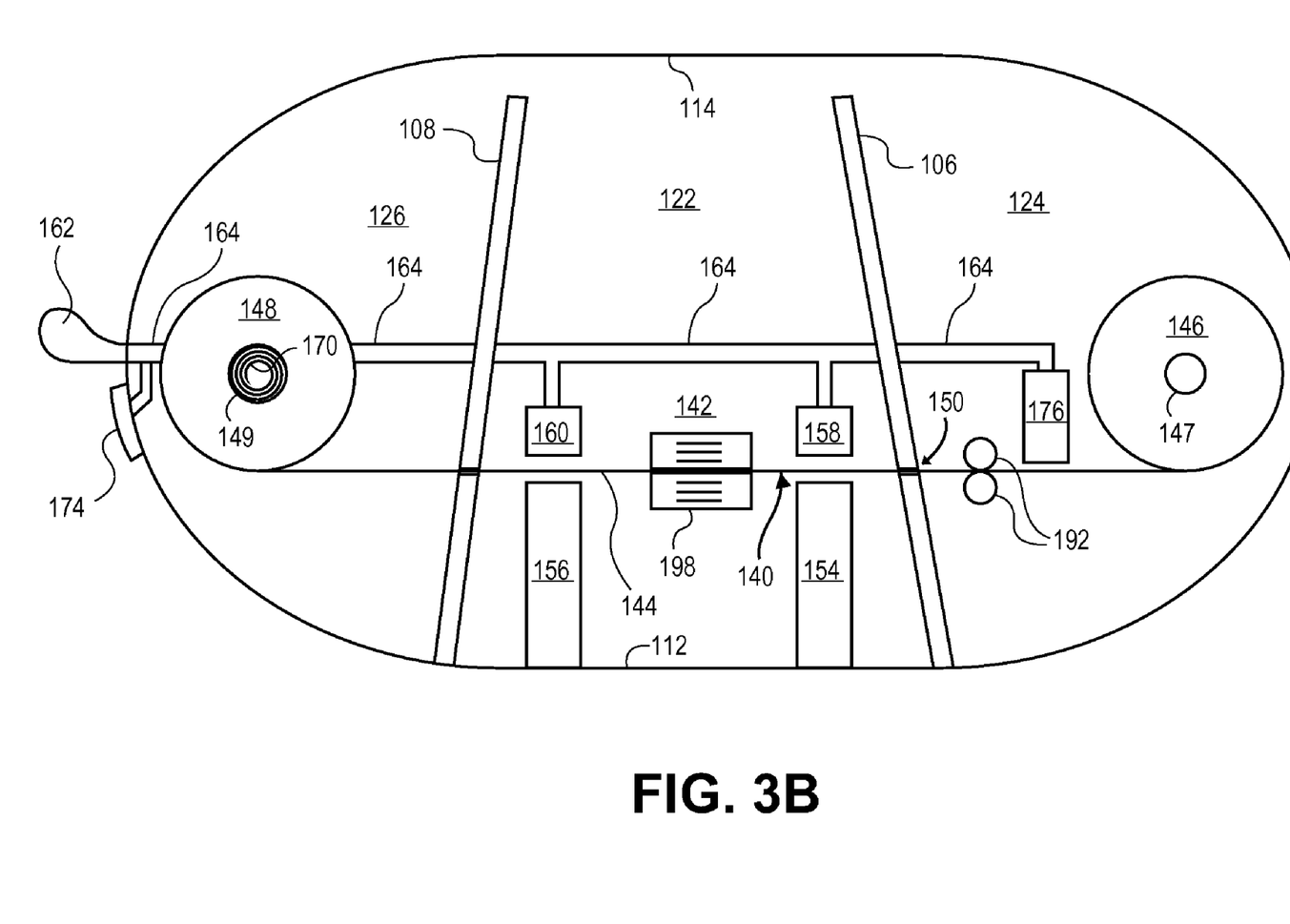
FIG. 3B is a schematic representation of an end cross-sectional view of an exemplary inhaler in accordance with various aspects of the disclosure.
Figure 4:
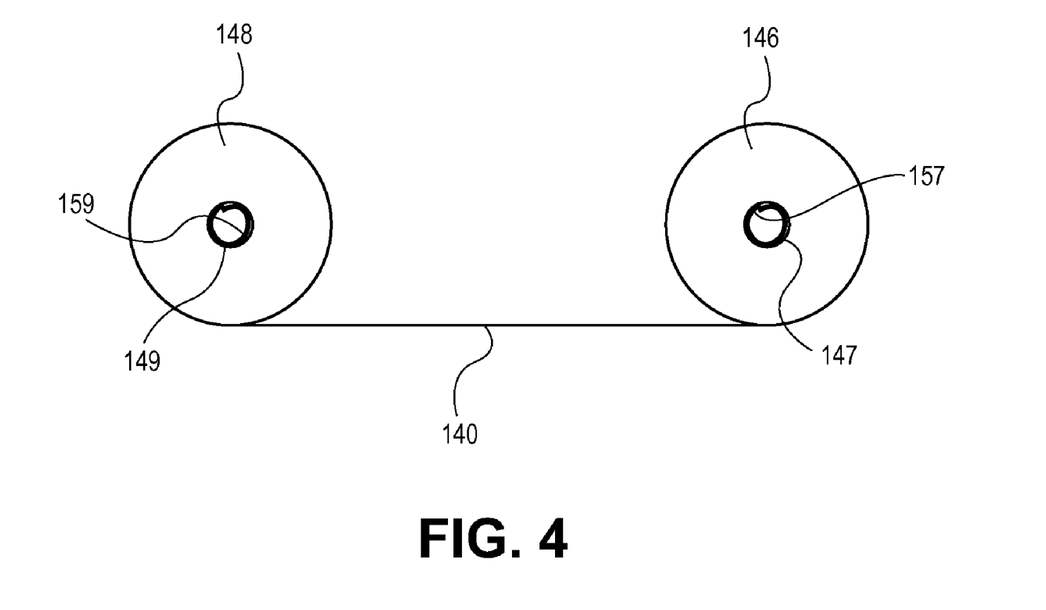
FIG. 4 is a schematic representation of first and second rollers loaded with the aeroelastic membrane with axles in the center of the rollers in accordance with various aspects of the disclosure.
Figure 5:
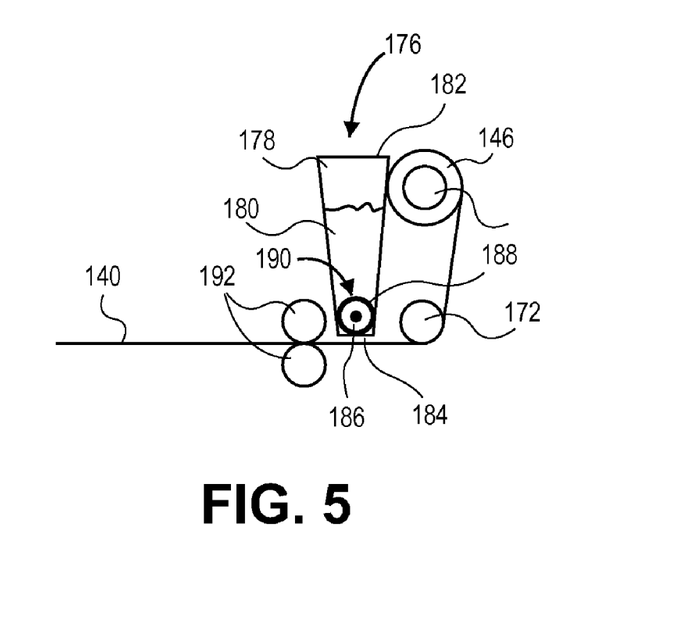
FIG. 5 is representation of an exemplary dosing applicator in accordance with various aspects of the disclosure.
Figure 6:
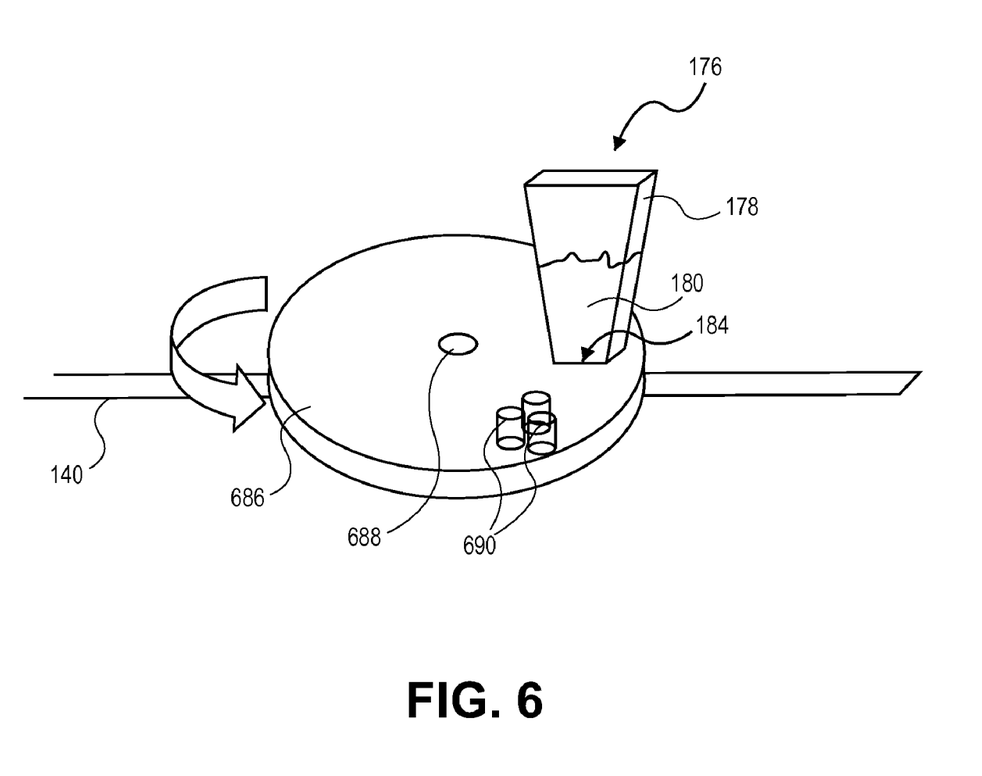
FIG. 6 is a representation of another exemplary dosing applicator in accordance with various aspects of the disclosure.

An exemplary embodiment of a dry powder inhaler 100 is illustrated in FIGS. 3A and 3B. According to various aspects of the disclosure, the dry powder inhaler 100 may comprise a casing 102 having an outer wall 104 and two inner walls 106, 108. The inner walls 106, 108 may extend in a first direction from a first inner surface 112 of the outer wall 104 toward a second inner surface 114 of the outer wall 104. The inner walls 106, 108 may also extend in a second direction from a proximal end 116 of the casing 102 to a distal end 118 of the casing 102. Thus, according to various aspects, the outer wall 104 and inner walls 106, 108 may cooperate to define three chambers in the casing 102.

According to some aspects, the three chambers may include a middle chamber 122 and two side chambers 124, 126 located on opposite sides of the middle chamber 122 relative to one another. The side chambers may comprise a first side chamber 124 located to a first side of the middle chamber 122 and a second side chamber 126 located to a second side of the middle chamber 122.

In accordance with various aspects, the distal end 118 of the casing 102 may include one or more airflow inlets 128 providing fluid communication between the middle chamber 122 and ambient air outside the casing 102. The proximal end 116 of the casing 102 may include a mouthpiece 130. The mouthpiece 130 may a separate structure affixed to the outer wall 104 of the casing 102, or the mouthpiece 130 and casing 102 may comprise a single piece of unitary construction. The mouthpiece 130 may include an opening 132 providing fluid communication between the middle chamber 122 and the outside of the casing 102. The opening 132 may be shaped as an oval, a circle, a triangle, or any other desired shape. The mouthpiece 130 may have a shape that facilitates pursing of a patient's lips over the mouthpiece 130 and creating a seal between the lips and the mouthpiece 130.

The inhaler 100 may include a nozzle 134 between the middle chamber 122 and the opening 132. According to various aspects, the nozzle 134 may extend from the opening 132, through the mouthpiece 130, and into the middle chamber 122. In some aspects, the nozzle 134 may comprise at least one helical tube 136 through which air and powder can be inhaled. The tube 136 can be configured to increase the turbulence in the air that flows through the nozzle 134.

An aeroelastic element 140 may extend across a center region 142 of the middle chamber 122 between the inner walls 106, 108. The aeroelastic element 140 may include one or more doses of a medicament 141, for example, doses of powdered medicament, and the center region 142 may comprise a region for dispensing a dose of medicament into airflow through the inhaler 100. According to some aspects, the aeroeslastic element 140 may comprise a membrane 144, for example, a thin elastic membrane, wound between two spools 146, 148. An unused end of the membrane 144 may be wound on a first spool 146, and a used end of the membrane 144 may be wound on a second spool 148. The first spool 146 may be disposed about a first axle 147, and the second spool 148 may be disposed about a second axle 149. The first spool 146 may be in the first side chamber 124, and the second spool 148 may be in the second side chamber 126. In such an embodiment, the membrane 144 extends through a slot 150 in the inner wall 106, across the center region 142, and through a slot 152 in the inner wall 108. In accordance with some aspects, the aeroelastic element 140 may comprise a membrane, a film, a reed, a sheet, a panel, or a blade. The aeroelastic element may be manufactured of materials comprising polymers, thin metals, polymer-coated metals, and/or metal-coated polymers.

According to various aspects, the inhaler 100 may include two base clamps 154, 156 fixedly attached to a first inner surface 112 of the casing 102. According to some aspects, the base clamps 154, 156 may be in the middle chamber 122. A first of the base clamps 154 may be between the center region 142 and the first inner wall 106, and the second of the base clamps 156 may be between the center region 142 and the second inner wall 108. The aeroelastic element 140 may rest on the base clamps 154, 156. The inhaler 100 may include two upper clamps 158, 160 in the middle chamber 122 associated with the two base clamps 154, 156. For example, a first upper clamp 158 may be on an opposite side of the aeroelastic element 140 relative to the first base clamp 154 and configured to descend atop the first base clamp 154 to sandwich the aeroelastic element therebetween. Similarly, the second upper clamp 160 may be on an opposite side of the aeroelastic element 140 relative to the second base clamp 156 and configured to descend atop the second base clamp 156 to sandwich the aeroelastic element therebetween. The upper clamps 158, 160 and base clamps 154, 156 may hold the aeroelastic element 140 in place across the center region 142 with a desired amount of tension. The desired amount of tension may be determined based on a user's inhalation strength. It should be appreciated that in some aspects, the upper clamps may be fixedly attached to the second inner surface 114 of the casing 102, and the base clamps may be configured to ascend toward the upper clamps to sandwich the aeroelastic element therebetween.

In an alternative embodiment (not shown), a first of the base clamps 154 may be in the first side chamber 124 between the first spool 146 and the first wall 106, and the second of the base clamps 156 may be in the second side chamber 126 between the second spool 148 and the second wall 108.

The inhaler 100 may include an advancement member 162 extending outward of the casing 102. The advancement member 162 may comprise, for example, a lever, a dial, or the like. The advancement member 162 may be mechanically coupled to the first and second upper clamps 158, 160 via, for example, a crank 164 or other known linkage. The advancement member 162 and crank 164 are structured and arranged such that when the advancement member 162 is actuated by a user, the crank 164 is caused to move the upper clamps 158, 160 in a direction away from the base clamps 154, 156. Actuation of the advancement member 162 may also cause the second axle 149 to turn in a manner that increases the used end of the aeroelastic element 140 wound thereon.

Figure 7A:
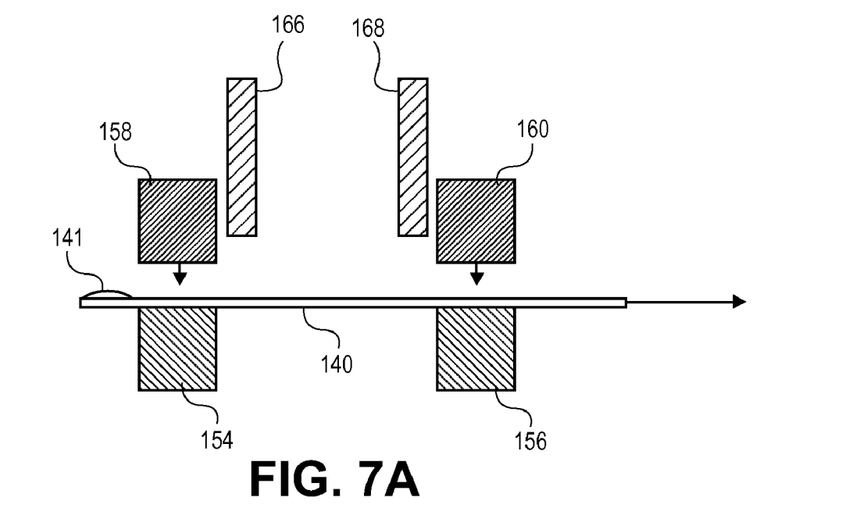
FIGS. 7A-7C are representations of an exemplary aeroelastic membrane and its relation to exemplary base clamps, upper clamps, and tensioning rods in accordance with various aspects of the disclosure.
Figure 7B:
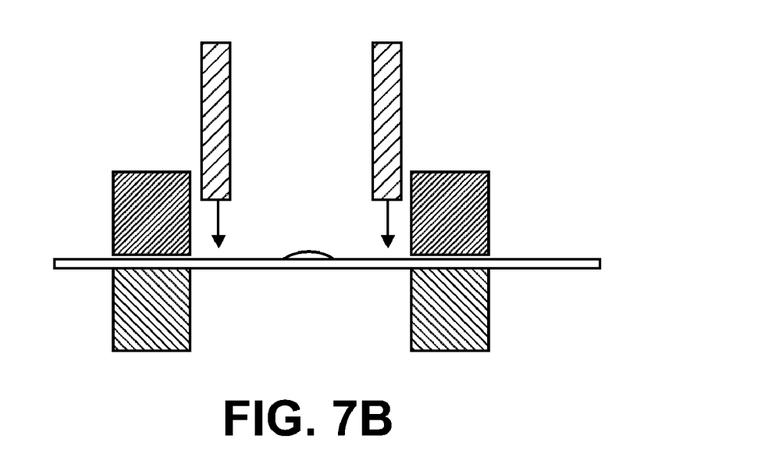
Figure 7C:
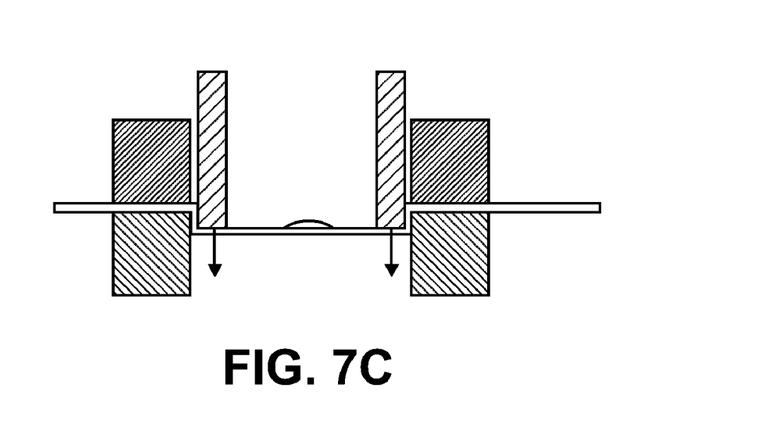
Figure 8:
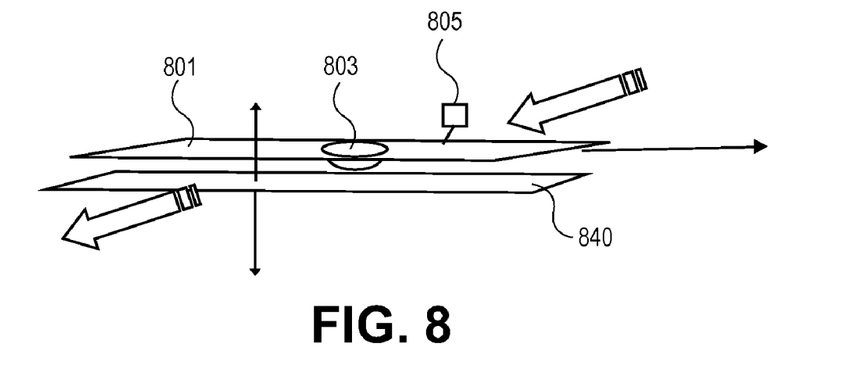
FIG. 8 is a representation of an exemplary dispensing mechanism in accordance with various aspects of the disclosure.
Figure 9:
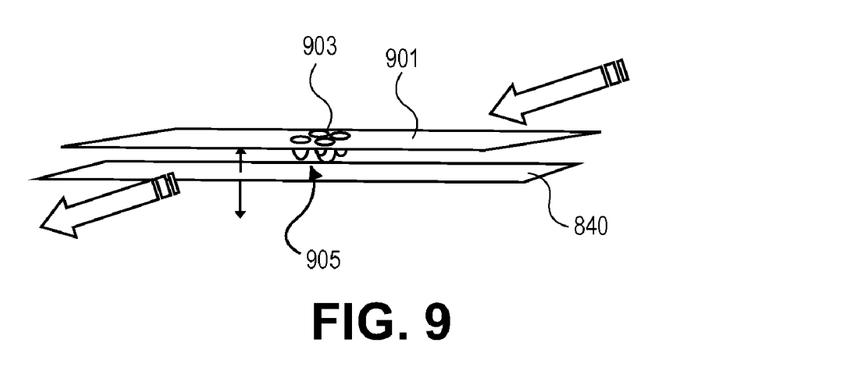
FIG. 9 is a representation of an alternative exemplary dispensing mechanism in accordance with various aspects of the disclosure.
Figure 10:
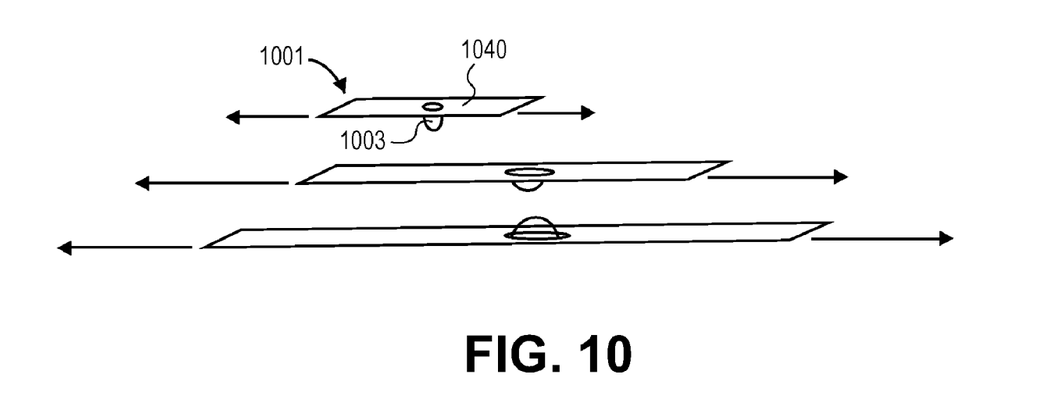
FIG. 10 is a representation of an alternative exemplary dispensing mechanism in accordance with various aspects of the disclosure.

According to some exemplary aspects, as shown in FIGS. 7A-7C, the inhaler 100 may include one or more tensioning rods 166, 168 configured to increase the tension of the aeroelastic element 140 beyond the tension applied by the base clamps 154, 156 and upper clamps 158, 160. The tensioning rods 166, 168 are between the first and second upper clamps 158, 160. The tensioning rods 166, 168 may be mechanically coupled to the crank 164 such that actuation of the advancement member 162 causes the tensioning rods 166, 168 to move in a direction away from the aeroelastic element 140. When the advancement member 162 is released or unactuated, the tensioning rods 166, 168 return to a position that applies a desired amount of tension to the aeroelastic element 140. It should be appreciated that in some aspects, one or more tension controllers 157, 159 (FIG. 4) may be attached to one or both of the spool axles 147, 149, thus allowing the tension of the aeroelastic element 140 to be manually fixed and maintained across the spool axles 147, 149 and obviating the need for tensioning rods. In any design, the amount tension applied by the clamps, tensioning rods, and/or tension controllers can be determined based on inhalation strength of a user.

Referring again to FIG. 3B, in various aspects, the second axle 149 associated with the second spool 148 may comprise a concentric spring 170, which is mechanically coupled to the advancement member 162 so that actuation of the advancement member 162 results in the aeroelastic element 140 being transferred from the first spool 138 to the second spool 148 as the spring-loaded axle 149 is activated. The inhaler 100 may include a roller 172 (FIG. 5) adjacent to the first spool 146 and engaging the aeroelastic element 140, thereby resulting in additional tension in the aeroelastic element.

According to some aspects, for example, inhalers having an aeroelastic element with multiple doses of medicament, a dose counter 174 may be mechanically coupled to the advancement member 162 in such a way that the dose counter 174 changes numbers by one each time the advancement member 162 is actuated. In some aspects, the dose counter 174 may be at an exterior surface of the casing 102 so as to be visible to a user. In some aspects, the dose counter 174 may be inside the casing 102, but visible to a user via a transparent or translucent window (not shown), as would be understood by persons skilled in the art.

According to various aspects, as shown in FIG. 5, the inhaler 100 may include a powder dose applicator 176 located between the first spool 146 and the first base clamp 154. In some aspects, the powder dose applicator 176 may include a dispensing chute 178 filled with at least one dose of powder 180. The dispensing chute 178 may include a top end 182 and a bottom end 184. A wheel 186 may be at the bottom end of the dispensing chute 178. The wheel 186 may be rotatable about an axle 188. The axle 188 may be mechanically coupled to the advancement member 162 such that the wheel 186 rotates an amount sufficient to dispense one dose of powdered medicament to the aeroelastic element. For example, the wheel 186 may include one or more notches 190 in its periphery, with the volume of each notch being sized for one dose of powdered medicament.

According to some aspects, the wheel shown in FIG. 5 may be replaced with a dispensing disk 686, as shown in FIG. 6. For example, the dispensing chute 178 above the aeroelastic element 140 is filled with at least one dose of powdered medicament. The dispensing disk 686 may be located between the aeroelastic element 140 and the dispensing chute 178 and may be in contact with the bottom end 184 of the chute 178. The disk 686 may further include multiple dispensing openings 690 clustered in one section of the disk 686, for example, a periphery of the disk 686. The dispensing openings 690 correspond to an accurate amount of powdered medicament to be dispensed as a dose. The dispensing disk 686 rotates about an axle 688 as the advancement member 162 is actuated, thereby resulting in an accurate amount of powdered medicament falling through the dispensing openings 690 and to the aeroelastic element 140. For example, the disk 686 may make one complete 360° rotation each time the advancement member 162 is actuated.

In various aspects, the inhaler 100 may include blister strip packaging attached to the two spools in place of the powder dose applicators discussed above. For example, as shown in FIG. 8, the blister strip packaging 801 may include at least one individual dosing cup 803. Each cup 803 may be filled with a dose of powdered medicament and covered by a peelable top layer. The dosing cups 803 may be arranged serially along the length of the packaging strip 801. An aeroelastic element 840 may be stretched across the center region 142 and fixedly coupled to, for example, the inner walls or any other structure capable of maintaining the element 840 fixedly stretched across the center region 142. The strip 801 may be in proximity to the aeroelastic element 840 in the center region 142 such that the aeroelastic element 840 may act as an actuator, making contact with the blister packaging and dispersing the powder dose when the aeroelastic element begins to vibrate during inhalation by a patient. A powder dose opener 805 may be configured to remove the top peelable layer from the blister strip packaging 801 for one dose when the blister strip 801 is advanced from the first spool to the second spool. The powder dose opener may alternatively be a simple puncturing device, such as a needle, that inserts small holes in the blister strip blister cavity, making the dose ready for inhalation.

In some embodiments, as shown in FIG. 9, blister strip packaging 901 may include clusters 905 of multiple small dosing cups 903 for simultaneous multiple drug dosing, the clusters 905 may be arranged serially along the length of the blister strip 901. The large arrows depict the direction of airflow across the blister strip and aeroelastic element. The small vertical arrows depict the vibrational motion of the aeroelastic element. In various embodiments, as shown in FIG. 10, the inhaler may include an aeroelastic element 1040 that may comprise, for example, an aeroelastic and deformable membrane. The element 1040 may include at least one individual dosing cup 1003 filled with a dose of powdered medicament in the form of blister strip packaging 1001. The dosing cup 1003 may be configured to deform and raise the powder dose to the level of the surrounding element 1040.

It should be appreciated that the inhaler may comprise a single powder dose such that the inhaler may be disposed of after a single use.

Referring again to FIG. 5, in some aspects, the inhaler 100 may include two rollers 192, one above and one below the aeroelastic element 140. The rollers 192 may be between the powder dose applicator 176 and the first base clamp 154 or between the powder dose applicator 176 and the inner wall 106. The rollers 192 turn as the aeroelastic element 140 moves from the first spool 146 to the second spool 148 due to the frictional force applied by the aeroelastic element 140 as it is urged past the pinching rollers 192. The rollers 192 fully engage the aeroelastic element 140 and flatten the powder deposited onto the aeroelastic element 140 and break up clumps in the powder.

Thus, the advancement member 162 may be capable of turning the crank to release the upper clamps and tensioner rods, advancing the dose counter, turning the wheel in the dispensing chute, advancing the spring-loaded axle in the second spool by one position to advance the aeroelastic element a predetermined distance from the first spool to the second spool, and/or moving a dose of powder medicament into the center region 142.

Referring again to FIGS. 3A and 3B, according to various aspects, the inhaler 100 may include one or more airflow modifiers 198 proximal of the one or more airflow inlets 128 and at a distal end of the center region 142. It should be appreciated that the one or more airflow modifiers 198 may be distal of the center region 142 and/or at a distal portion within the center region 142. In some aspects, the one or more airflow modifiers 198 may comprise multiple triangular rods extending from the first inner wall 106 to the second inner wall 108. As air flows through the one or more airflow inlets 128 and toward the center region 142, the one or more airflow modifiers 198 may cause vortices that allow air to pass above and below the modifiers.

Figure 1:
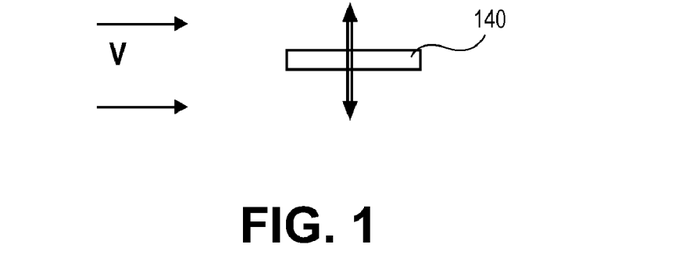
FIG. 1 illustrates airflow across an aeroelastic element in accordance with various aspects of the disclosure.
Figure 2:
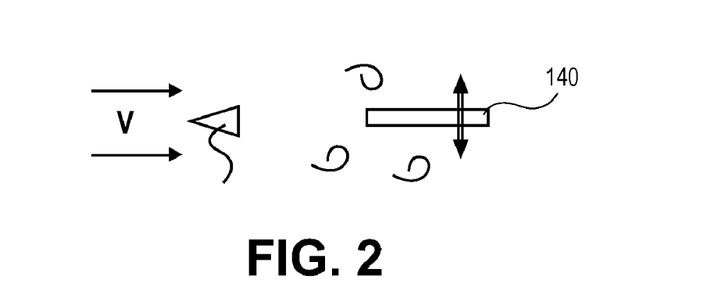
FIG. 2 illustrates airflow past an airflow modifier and across an aeroelastic element in accordance with various aspects of the disclosure.

Referring now to FIG. 1, airflow at velocity V over an aeroelastic element under tension is illustrated. As shown, the airflow may result in flutter or vibration of the aeroelastic element 140. The vibration is represented by vertical arrows, and the airflow is represented by horizontal arrows. FIG. 2 illustrates the airflow at velocity V past an airflow modifier prior to encountering an aeroelastic element 140. As shown, the airflow modifier introduces turbulence into the airflow, thus increasing the vibration or flutter of the aeroelastic element for a given inhalation strength.

In operation, a method for dispensing powder by inhalation using any of the aforementioned exemplary dry powder inhaler apparatuses may begin with a patient actuating the advancement member. The patient may purse his/her lips around the mouthpiece and inhales. As the patient inhales, air is sucked into the inhaler through one or more airflow inlets at the distal end of the inhaler. The inhaled air flows over the airflow modifiers. The airflow then encounters the aeroelastic element, causing the element to vibrate or flutter and disperse a dose of powdered medicament from the element into the airflow. The combined flow of air and powder then flow into the distal end of the airflow nozzle and the mouthpiece. The combined flow of air and powder leave the mouthpiece and enter the patient's mouth and respiratory tract. The airflow modifiers and/or the helical shape of the nozzle may increase the turbulence of the airflow to better aerosolize and break up the powdered dose of medicament into smaller particles, thus maximizing the dose received by the patient and allowing the smaller particles to pass further into the respiratory tract.

It will be apparent to those skilled in the art that various modifications and variations can be made in the inhalers and methods of the present disclosure without departing from the scope of the invention. Other embodiments of the invention will be apparent to those skilled in the art from consideration of the specification and practice of the invention disclosed herein. It is intended that the specification and examples be considered as exemplary only.

What is claimed is:

1. A dry powder inhaler for delivering medicament to a patient, the inhaler comprising:
   a housing defining a chamber for receiving a dose of powdered medicament;
   an inhalation port in fluid communication with the chamber;
   at least one airflow inlet providing fluid communication between the chamber and an exterior of the housing;
   an aeroelastic element in the chamber and associated with a dose of powdered medicament; and
   a tensioning assembly including
      a first tensioning arrangement and a second tensioning arrangement on opposite sides of the chamber with the aeroelastic element extending therebetween, the first and second tensioning arrangements being configured to apply a first amount of tension to the aeroelastic element such that the aeroelastic element is capable of vibrating in response to airflow through the chamber so as to aerosolize the dose of powdered medicament, and
      a third tensioning arrangement movable relative to the aeroelastic element, the third tensioning arrangement being configured to apply a second amount of tension to the aeroelastic element, the second amount of tension being greater than the first amount of tension.

2. The device of claim 1, wherein the tensioning assembly comprises two pairs of clamps, said pairs of clamps being on opposite sides of the chamber each of the first and second tensioning arrangements includes a pair of clamps.

3. The device of claim 2, wherein each pair of clamps comprises clamping members on opposite sides of the aeroelastic element.

4. The device of claim 1, wherein the second amount of tension produces a desired vibration of the aeroelastic element in response to airflow rates of a patient.

5. The device of claim 1, wherein the first amount of tension produces a desired vibration of the aeroelastic element in response to airflow rates of a patient.

6. The device of claim 1, further comprising an airflow modifier between said at least one airflow inlet and the aeroelastic element, the airflow modifier causing airflow disturbance, wherein the airflow disturbance assists with aerosolizing the dose of powdered medicament.

7. The device of claim 1, wherein the aeroelastic element comprises one of a membrane, a reed, a sheet, a panel, and a blade.

8. The device of claim 1, wherein the aeroelastic element is made of a material comprising at least one of a polymer, a metal, a polymer-coated metal, and a metal-coated polymer.

9. The device of claim 1, further comprising:
   a mouthpiece including the inhalation port; and
   a nozzle between the chamber and the inhalation port.

10. The device of claim 1, further comprising:
    a pair of spools, one on each side of the chamber, the aeroelastic element being coupled to said spools and extending across the chamber in a direction substantially perpendicular to a path of airflow from said at least one airflow inlet to the inhalation port; and
    at least one tension controller, each said tension controller coupled to an axle of one of said spools so as to permit manual tensioning of the aeroelastic element via the spool axles.

11. The device of claim 1, wherein the aeroelastic element comprises an aeroelastic and deformable membrane including at least one dosing cup filled with a dose of powdered medicament, the dosing cup being configured to deform and raise the powder dose to a level of the membrane when in the chamber.

12. A dry powder inhaler for delivering medicament to a patient, the inhaler comprising:
- a housing defining a chamber for receiving a dose of powdered medicament;
- an inhalation port in fluid communication with the chamber;
- at least one airflow inlet providing fluid communication between the chamber and an exterior of the housing;
- an aeroelastic element in the chamber and associated with a dose of powdered medicament:
- a tensioning assembly including: a first tensioning arrangement and a second tensioning arrangement on opposite sides of the chamber with the aeroelastic element extending therebetween, the first and second tensioning arrangements being configured to apply a first amount of tension to the aeroelastic element such that the aeroelastic element is capable of vibrating in response to airflow through the chamber so as to aerosolize the dose of powdered medicament, and a third tensioning arrangement movable relative to the aeroelastic element, the third tensioning arrangement being configured to apply a second amount of tension to the aeroelastic element, the second amount of tension being greater than the first amount of tension; and a powder dose applicator,
- the powder dose applicator being configured to dispense the dose of powdered medicament to the aeroelastic element prior to inhalation by a patient.

13. The device of claim 12, further comprising an advancement member mechanically coupled to the clamps and the powder dose applicator.

14. The device of claim 13, wherein the advancement member is configured such that actuation of the advancement member moves the clamps away from the aeroelastic element, causes the powder dose applicator to dispense a dose to the aeroelastic element, and moves the aeroelastic element to bring said dispensed dose into the chamber.

15. The device of claim 14, wherein the tensioning assembly further comprises at least one tensioning member configured to apply a second amount of tension to the aeroelastic element, the second amount of tension being greater than the first amount of tension.

16. The device of claim 15, wherein the advancement member is mechanically coupled to the at least one tensioning member such that actuation of the advancement member moves the at least one tensioning member away from the aeroelastic element to remove the second amount of tension.

17. The device of claim 16, further comprising a dose counter, the advancement member being mechanically coupled to the dose counter such that actuation of the advancement member moves the dose counter to indicate the number of doses of powdered medicament remaining in the device.

18. The device of claim 1, further comprising a strip extending across the chamber substantially parallel to the aeroelastic element, the strip containing at least one pre-metered quantity of the dose of powdered medicament, the strip and the aeroelastic element being in close proximity to one another such that vibration of the aeroelastic element causes aerosolization of the dose of powdered medicament.

19. The device of claim 18, wherein the strip comprises a plurality of clusters of dosing cups, each cluster of dosing cups comprising a dose of powdered medicament to be aerosolized.

20. A dry powder inhaler for delivering medicament to a patient, the inhaler comprising:
- a housing defining a chamber for receiving a dose of powdered medicament;
- an inhalation port in fluid communication with the chamber;
- at least one airflow inlet providing fluid communication between the chamber and an exterior of the housing;
- an aeroelastic element in the chamber and associated with a dose of powdered medicament;
- a tensioning assembly including: a first tensioning arrangement and a second tensioning arrangement on opposite sides of the chamber with the aeroelastic element extending therebetween, the first and second tensioning arrangements being configured to apply a first amount of tension to the aeroelastic element such that the aeroelastic element is capable of vibrating in response to airflow through the chamber so as to aerosolize the dose of powdered medicament, and a third tensioning arrangement movable relative to the aeroelastic element, the third tensioning arrangement being configured to apply a second amount of tension to the aeroelastic element, the second amount of tension being greater than the first amount of tension; and an airflow modifier
- between said at least one airflow inlet and the aeroelastic element, the airflow modifier causing airflow disturbance, wherein the airflow disturbance assists with aerosolizing the dose of powdered medicament.

* * * * *